United States Patent
McCormick et al.

(10) Patent No.: US 6,929,617 B2
(45) Date of Patent: *Aug. 16, 2005

(54) NONBULKY ANKLE BRACE FOR USE WITH FOOTWEAR

(75) Inventors: Scott D. McCormick, Cincinnati, OH (US); Sherry Hinds, Goshen, OH (US)

(73) Assignee: Beiersdorf Inc., Wilton, CT (US)

( * ) Notice: Subject to any disclaimer, the term of this patent is extended or adjusted under 35 U.S.C. 154(b) by 80 days.

This patent is subject to a terminal disclaimer.

(21) Appl. No.: 10/175,214

(22) Filed: Jun. 18, 2002

(65) Prior Publication Data

US 2003/0233062 A1 Dec. 18, 2003

(51) Int. Cl.$^7$ ................................................ A61F 5/00
(52) U.S. Cl. ........................ 602/65; 602/27; 128/882
(58) Field of Search ........................ 602/65, 62, 61, 602/60, 41, 27; 128/882

(56) References Cited

U.S. PATENT DOCUMENTS

| | | | |
|---|---|---|---|
| 3,050,053 A | | 8/1962 | Peckham |
| 3,073,305 A | * | 1/1963 | Biggs, Jr. et al. ............. 602/65 |
| 4,323,058 A | * | 4/1982 | Detty ........................... 602/27 |
| 4,378,793 A | | 4/1983 | Mauldin et al. |
| 4,414,965 A | | 11/1983 | Mauldin et al. |
| 4,446,856 A | | 5/1984 | Jordan |
| 4,572,169 A | | 2/1986 | Mauldin et al. |
| 4,630,600 A | * | 12/1986 | Spencer et al. ............... 602/27 |

(Continued)

FOREIGN PATENT DOCUMENTS

| | | |
|---|---|---|
| DE | 201 15 104 U 1 | 3/2002 |
| GB | 2 241 170 | 8/1991 |

*Primary Examiner*—Gregory L. Huson
*Assistant Examiner*—Huong Q. Pham
(74) *Attorney, Agent, or Firm*—Alston & Bird LLP (57) ABSTRACT

An ankle brace for comfortably supporting an ankle of a wearer by inhibiting motion between a foot and lower leg of the wearer. The ankle brace employs a laminated, moisture-wicking material for leg and foot portions that improves wearability during athletic activities. The leg and foot portions are combined with medial and lateral stays that are supported within pockets of the leg portion so as to provide medial and lateral stability for the ankle. A strapping unit is used to further improve stability with a pair of straps that are formed of the same piece of laminate material as the foot portion and extend upwards from the foot portion to cross over the ankle and attach to the leg portion. Advantageously, constructing the straps from the same piece of material as the foot portion eliminates fasteners and overlapping material and allows the ankle brace to be used with off-the-shelf footwear.

20 Claims, 8 Drawing Sheets

U.S. PATENT DOCUMENTS

| | | | |
|---|---|---|---|
| 4,651,726 A | | 3/1987 | Holland |
| 4,729,370 A | * | 3/1988 | Kallassy ............... 602/65 |
| 4,825,856 A | * | 5/1989 | Nelson ................. 602/27 |
| 4,878,504 A | * | 11/1989 | Nelson ................. 602/27 |
| 4,974,583 A | * | 12/1990 | Freitas ................. 602/24 |
| 4,998,537 A | | 3/1991 | Rau |
| 5,000,195 A | * | 3/1991 | Neal ..................... 602/27 |
| 5,067,486 A | | 11/1991 | Hely |
| 5,090,404 A | * | 2/1992 | Kallassy ............... 602/65 |
| 5,160,314 A | * | 11/1992 | Peters .................. 602/21 |
| 5,217,431 A | | 6/1993 | Toronto et al. |
| 5,352,189 A | | 10/1994 | Schumann et al. |
| 5,393,303 A | * | 2/1995 | Shiono ................. 602/27 |
| 5,472,411 A | * | 12/1995 | Montag et al. ........ 602/23 |
| 5,472,414 A | * | 12/1995 | Detty ................... 602/27 |
| 5,609,570 A | * | 3/1997 | Lamont ................ 602/65 |
| 5,620,411 A | | 4/1997 | Schumann et al. |
| 5,620,413 A | * | 4/1997 | Olson ................... 602/65 |
| 5,657,767 A | * | 8/1997 | Nelson et al. ........ 128/882 |
| 5,713,837 A | | 2/1998 | Grim et al. |
| 5,741,222 A | | 4/1998 | Fiore |
| 5,795,316 A | | 8/1998 | Gaylord |
| 5,833,639 A | | 11/1998 | Nunes et al. |
| 5,833,640 A | | 11/1998 | Vazquez, Jr. et al. |
| D403,776 S | | 1/1999 | Brennan |
| 5,868,693 A | | 2/1999 | Duback et al. |
| 5,899,872 A | | 5/1999 | Gilmour |
| 5,925,010 A | * | 7/1999 | Caprio, Jr. ............ 602/62 |
| D412,581 S | | 8/1999 | Brennan |
| 5,944,678 A | | 8/1999 | Hubbard |
| 6,024,712 A | | 2/2000 | Iglesias et al. |
| 6,039,706 A | * | 3/2000 | Bolla et al. ............ 602/5 |
| 6,110,135 A | * | 8/2000 | Madow et al. ........ 602/20 |
| 6,117,098 A | * | 9/2000 | Weber et al. .......... 602/27 |
| 6,126,626 A | | 10/2000 | Duback et al. |
| 6,126,627 A | | 10/2000 | Brennan |
| 6,245,035 B1 | * | 6/2001 | Schrijver .............. 602/27 |
| 6,394,971 B1 | * | 5/2002 | Slautterback et al. ... 602/27 |
| 6,398,750 B1 | * | 6/2002 | Quinn et al. .......... 602/65 |
| 6,617,485 B2 | * | 9/2003 | Herzberg .............. 602/41 |
| 2002/0035344 A1 | * | 3/2002 | Herzberg |

* cited by examiner

NONBULKY ANKLE BRACE FOR USE WITH FOOTWEAR

BACKGROUND OF THE INVENTION

1) Field of the Invention

The present invention is related to the field of orthopedic braces, and in particular, braces for supporting the ankle of a wearer during sports and other activities.

2) Description of Related Art

Over the past few decades participation in various sports activities by both men and women has experienced explosive growth. The increase in participation has also led to an increase in the incidence of sports-related injuries. Many of these activities require high-speed running with rapid directional changes, or "cutting," such as soccer and football. Cutting motions subject an athlete's ankle joint to extremely large forces which may result in a traumatic injury. In addition, such forces over time tend to decrease the stability of the ankle joint by increasing the drawer, or range of anterior-posterior and medial-lateral sliding motion, of the foot with respect to lower leg. Instability in the ankle increases the risk of the eventual occurrence of a traumatic injury. Traumatic injury often occurs with inversion, or eversion, of the foot. Inversion occurs when the athlete plants her foot to resist a large lateral force and the athlete's foot rolls onto its lateral surface while the lower leg (or tibia) remains relatively upright. Eversion occurs in the opposite direction, where the athlete's foot rolls onto its medial surface. Both motions can result in a soft-tissue injury, such as a sprain, or even a bone fracture. For instance, inversion can result in a Weber fracture, which is a fracture of the distal fibula.

Various taping methods have been developed to increase the stability of an already-injured, or unstable, ankle joint. The application of tape, however, takes a significant amount of time and effort and may result in reduced circulation in the foot which is uncomfortable for the wearer. In addition, the tape cannot be easily removed, and when removed cannot be reapplied or reused. As a solution to this, ankle braces have been developed that typically include a canvas or leather sleeve extending over the ankle similar to the upper of a high-top basketball shoe with a plurality of laces and eyelets for a tensioned closure. Despite the additional support provided by such braces, tightening and loosening of the laces can be burdensome. In addition, canvas and leather are not very breathable materials causing the buildup of moisture during activities and making the brace uncomfortable for the wearer.

An ankle brace shown in FIGS. 6(a) and 6(b) of U.S. Pat. No. 5,393,303 to Shiono discloses a main body 1 constructed of a laminated, three-layer fabric and including a lower leg covering portion 2 and a foot covering portion 4 between which is defined a heel opening 13. The laminated fabric has a polyurethane, non-woven fabric as a core material, a "sweat-in" and "sweat-out" polyester fabric as the inner layer, and a polyamide stretch French pile as the outer layer. Two stretch belts 20, 21 extend over the foot and ankle and cross each other to attach to the French pile via VELCRO fasteners 20a and 21a, as shown in FIG. 1 of Shiono. Also, binding belts 15, 16, 17 and 18 wrap around and secure the shank portion of the main body to the leg. A pair of molded stays 22, 24 are mounted to the main body under the binding belts, as shown in FIGS. 3 and 4 of Shiono. The use of the laminated fabric for the main body improves the removal of moisture and sweat from the skin of the wearer. However, Shiono's ankle brace is too bulky for use with most footwear and therefore is of limited use to an active wearer wishing to prevent, as well as rehabilitate, an injury.

Therefore, it would be advantageous to have an ankle brace that is not too bulky to be useable with footwear during athletic activities. In addition, it would be advantageous to have an ankle brace that is comfortable to wear, especially during activities requiring exertion that produces heat and moisture within the brace. Further, it would be advantageous to have an ankle brace that combines comfortable wear with sufficient support to prevent ankle injuries.

BRIEF SUMMARY OF THE INVENTION

The present invention addresses the above needs and achieves other advantages by providing an ankle brace for comfortably supporting an ankle of a wearer by inhibiting motion between a foot and lower leg of the wearer. A foot portion and leg portion of the ankle brace are formed of a laminated, moisture-wicking material that improves wearability during athletic activities. The leg and foot portions are combined with medial and lateral stays that are supported within pockets of the leg portion so as to provide medial and lateral stability for the ankle. A strapping unit is used to further improve stability via a pair of straps that are formed of the same piece of laminate material as the foot portion and extend upwards from the foot portion to cross over the ankle and attach to the leg portion. Advantageously, constructing the straps from the same piece of material as the foot portion eliminates fasteners and their attendant bulk and allows the ankle brace to be used with off-the-shelf footwear.

In one embodiment, the present invention includes an ankle brace for comfortably supporting an ankle of a wearer by inhibiting motion between a foot and lower leg of the wearer. The ankle brace includes a leg portion constructed of a flexible sheet material configured to embrace the lower leg of the wearer and to extend distally along the lower leg to the ankle. The flexible sheet material defines an opening for receiving the lower leg of the wearer. Lateral and medial stays are constructed of a relatively rigid material and are configured to extend along portions of the lower leg, ankle and foot of the wearer. The lateral and medial stays are attached to the lateral and medial sides of the leg portion, respectively, so as to inhibit motion between the foot and lower leg of the wearer. The ankle brace also includes a strapping unit, comprising the aforementioned foot portion and a pair of cross-straps, constructed of a single piece of moisture-wicking, laminate sheet material. The foot portion is coupled to the leg portion at the ankle and is configured to extend along and under at least a portion of the foot. The cross-straps are configured to extend upwards from the foot portion and cross over each other at the ankle, attaching to the leg portion. Use of the strapping unit further inhibits relative motion of the foot and lower leg while the laminate sheet material wicks away moisture from the wearer's foot, ankle and lower leg.

In one aspect of the invention, each of the stays can include a rib or ribs extending along the stay so as to increase its rigidity. Further, the stays may each define a notch that is sized and shaped to receive the malleolus of the wearer. The leg portion can further include lateral and medial pockets configured to hold the lateral and medial stays, respectively.

Preferably, the laminate material includes an inner moisture-wicking ply, an outer elastic ply and a foam core between the inner and outer plies. The flexible sheet material of the leg portion may also be constructed of a laminate material having moisture-wicking properties. The leg and foot portions can be coupled by being stitched together along adjacent edges meeting at the ankle of the wearer.

The ankle brace may also include one or more lower leg straps that extend around the leg portion so as to bind it to the lower leg of the wearer. In one embodiment, loop material is disposed on the leg portion to provide a surface for attachment of each of the straps having ends with a hook material disposed thereon.

Wearer comfort, and the ability to insert the ankle brace into conventional footwear that has little front-to-back adjustability, can be further facilitated by the foot portion defining heel and toe openings.

Among other advantages, the ankle brace of the present invention supports the wearer's ankle while having minimal bulk and therefore being useable with conventional footwear. Further, the use of a single piece of laminate material for the strapping system eliminates the need for overlapping material or fasteners to attach the cross-straps to the foot portion. Elimination of the overlap and fasteners further reduces bulk and facilitates use of the ankle brace with footwear. Use of a laminate material with wicking properties keeps the ankle, foot and lower leg of the wearer dry during athletic activities. The optional rib on each of the stays improves the stiffness of the stay without adding appreciable weight or bulk to the ankle brace.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION OF THE INVENTION

The present inventions now will be described more fully hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Figure 1:
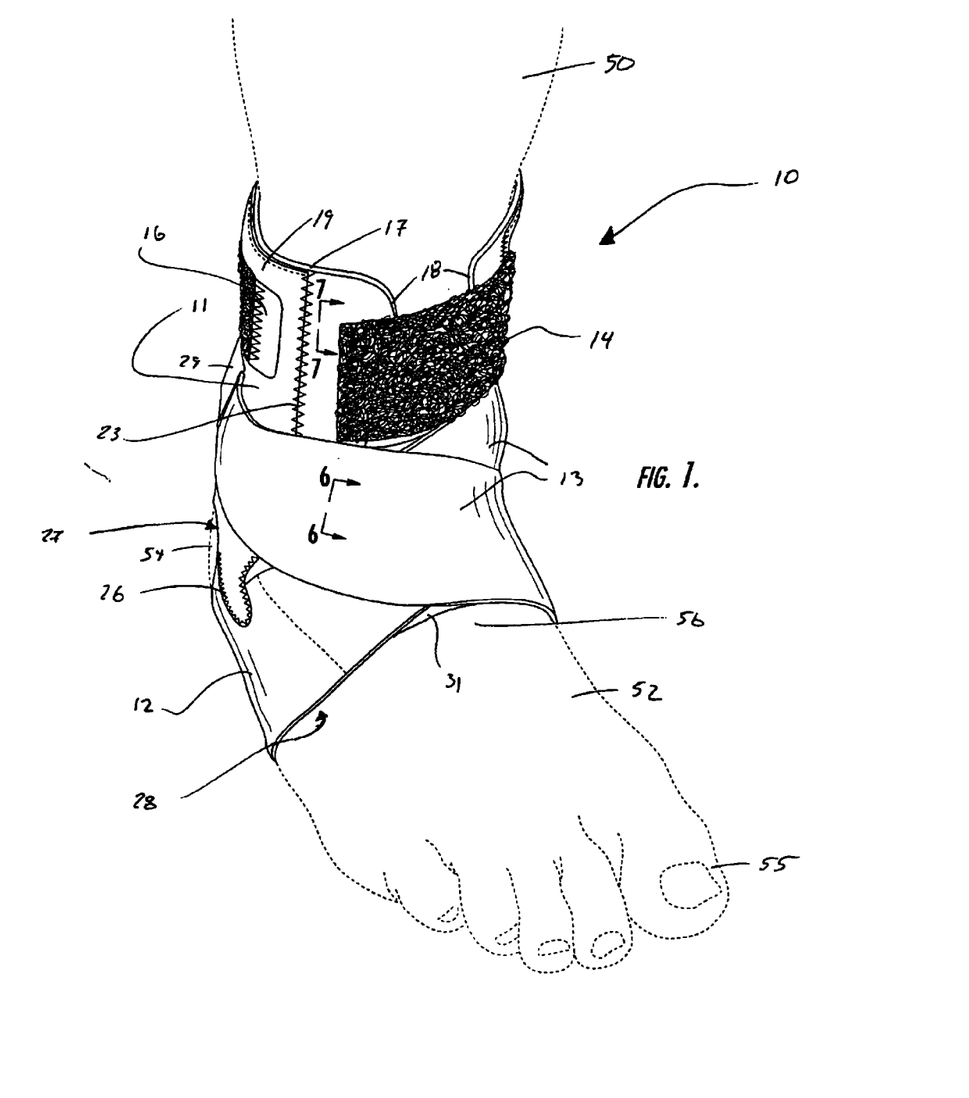
FIG. 1 is a perspective view of one embodiment of an ankle brace of the present invention secured to an ankle of a wearer.
Figure 2:
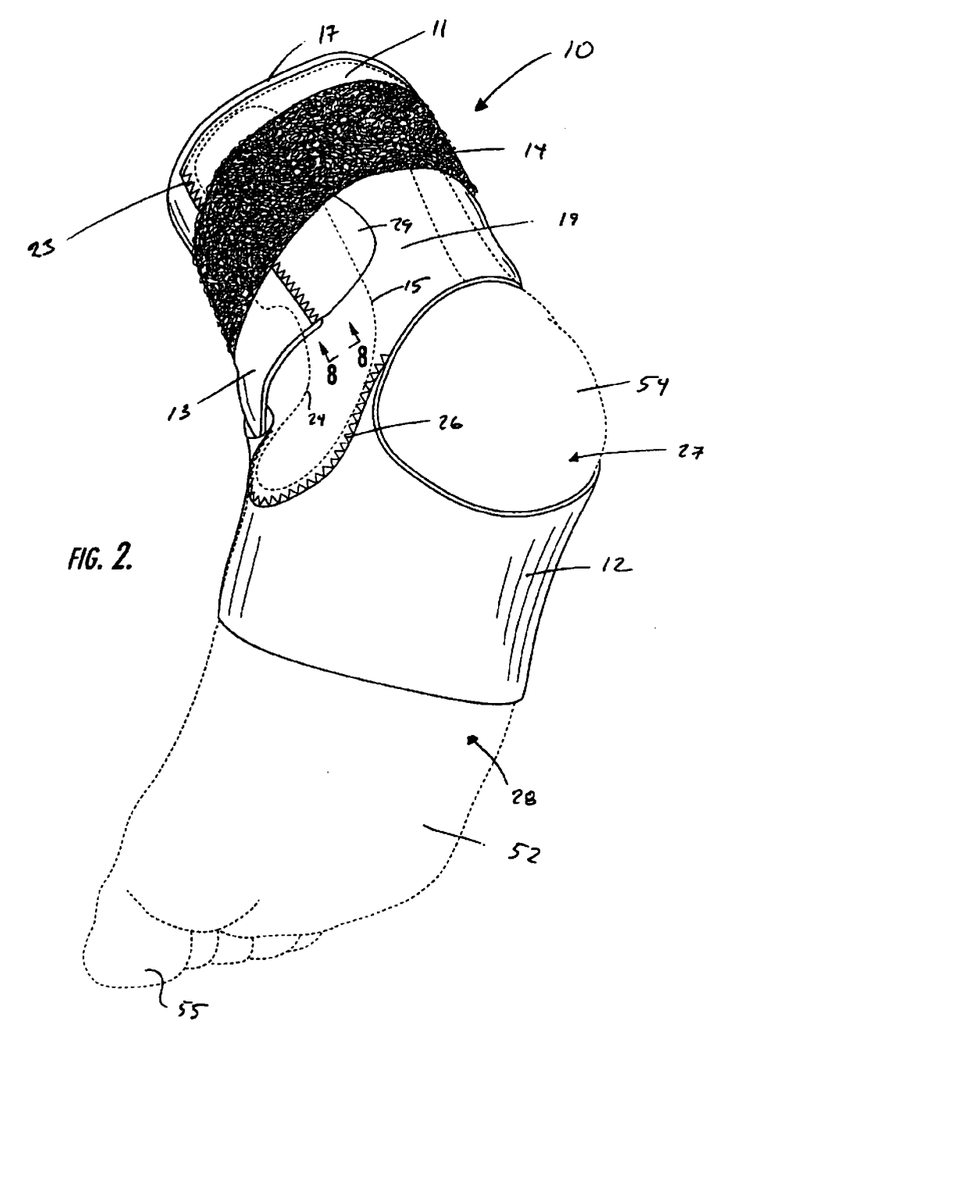
FIG. 2 is another perspective view of the ankle brace of FIG. 1.

An ankle brace 10 of one embodiment of the present invention is illustrated in FIGS. 1 and 2. The ankle brace includes a leg portion 11 extending along and embracing a lower leg 50 of the wearer. A foot portion 12 wraps under a portion of a foot 52 of the wearer and is attached to the leg portion 11 approximately at an ankle of the wearer. Extending upwards from the foot portion 12 are a pair of cross-straps 13 that cross over the ankle and attach to opposite sides of the leg portion 11. The ankle brace 10 is ambidextrous and can be used on either a left or right foot.

The leg portion 11 is formed of a sheet of flexible material and in the illustrated embodiments has the shape of a cuff, defining a top edge 17 and a pair of opposing front edges 18. The top edge 17 extends around the lower leg 50 of the wearer, preferably roughly at the midpoint of the lower leg, thereby encircling a large part of the wearer's calf. The pair of opposing front edges 18 extend downwards along the front of the wearer's shin and ankle. In combination, the top and front edges 17, 18 of the leg portion 11 define an opening for receiving the lower leg 50 therein in an embracing fit. The geometry of the leg portion 11 and its opening preferably allows it to fit a large number of persons, such as 20% of the female population and 95% of the male population. At a fit of 20% of the female population, the brace 10 forms about an 8 inch circle around the lower leg above the malleoli. At a fit of 95% of the male population, the brace forms about a 10 inch circle around the lower leg above the malleoli.

Figure 7:
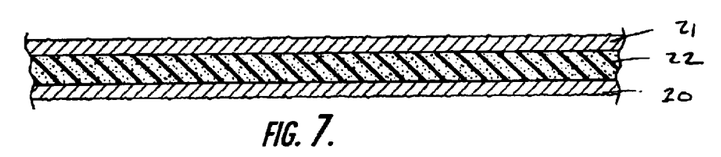
FIG. 7 is a sectional view of a laminate material used to construct a leg portion of the ankle brace shown in FIG. 1.

Preferably, the leg portion 11 is constructed of a laminate having multiple plies, including a soft, moisture-wicking material as its inner, skin-adjacent ply 20 and an outer ply 21, as shown in FIG. 7. The laminate of the leg portion 11 may also include a foam core 22 sandwiched between the skin-adjacent ply 20 and the outer ply 21. Preferable materials for the outer ply 21, core ply 22 and inner ply 20 are VELCRO laminates of ORTHOWICK (a lightly-napped tricot), 0.125 inch G45 and ORTHOWICK, respectively, or ORTHOWICK, 0.125 inch G45L (a urethane foam), tricot with zero stretch, respectively. Advantageously, the ORTHOWICK or tricot inner ply of the laminate is worn against the skin and has a low skin irritant, soft feel and moisture-wicking properties.

Figure 9:
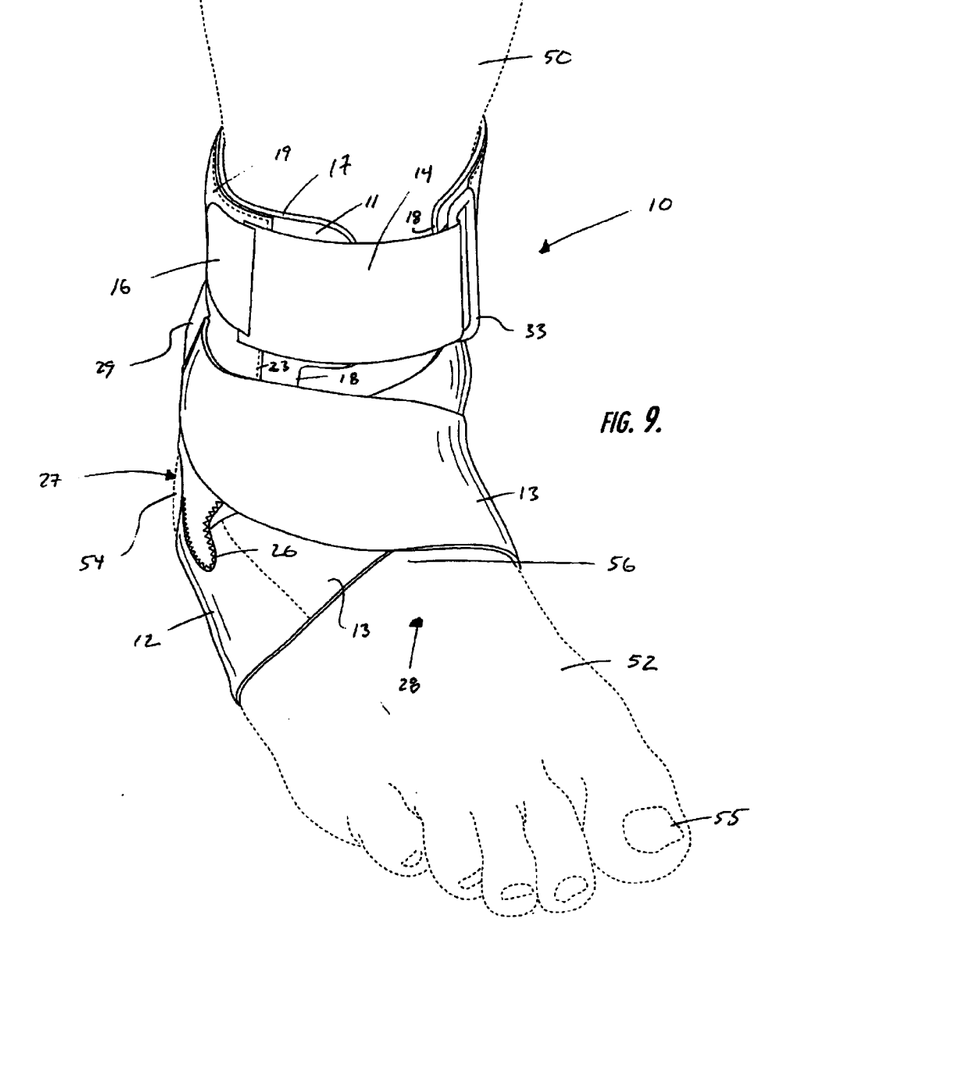
FIG. 9 is a perspective view of another embodiment of an ankle brace of the present invention.
Figure 10:
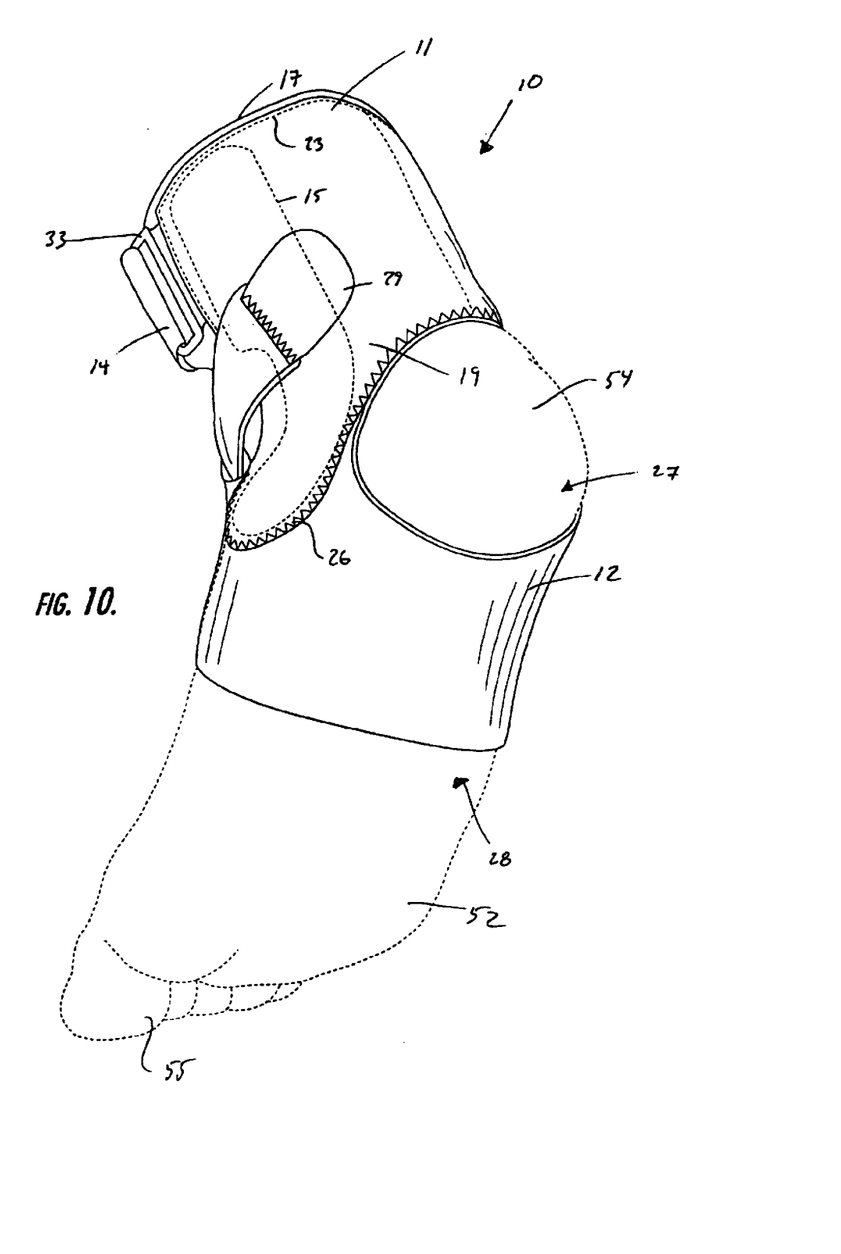
FIG. 10 is another perspective view of the ankle brace of FIG. 9.
Figure 11:
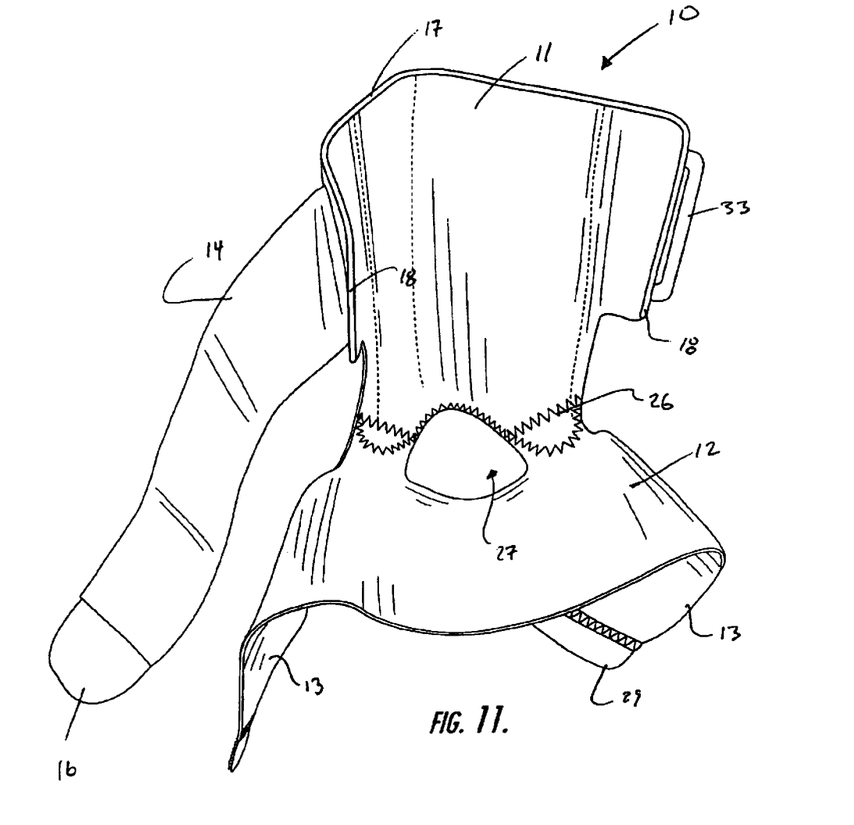
FIG. 11 is yet another perspective view of the ankle brace of FIG. 9, but opened and ready to receive the ankle of the wearer.

The ankle brace 10 may include a leg strap 14 that encircles the top of the leg portion 11, holding the front edges 18 together so that the leg portion 11 firmly embraces the lower leg 50 of the wearer. The leg strap 14 includes an elongate strip of material attached at one end to one of the front edges 18 and having a hook material pad or patch 16 on its other end. Optionally, on the opposite one of the front edges, across from the attachment of the leg strap 14, a buckle 33 can be attached having an opening therethrough sized to receive the free end of the leg strap 14, as shown in FIGS. 9–11. Once passed through the buckle 33, the strap 14 is reversed back on itself and pulled tight to draw the front edges 18 together. The strap 14 is wrapped around the leg 50 and its free end is secured via the hook material patch 16 to the loop material on a stay cover 19, which is in turn attached to the outer ply 21 of the leg portion 11.

Figure 8:
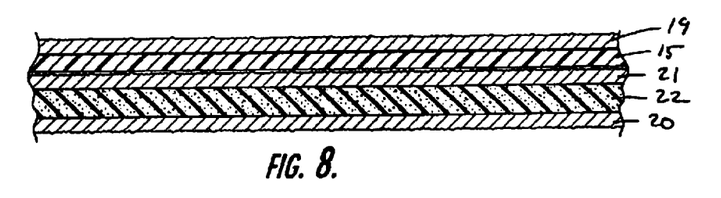
FIG. 8 is a sectional view of the laminate material of the leg portion shown in FIG. 7, the stay of FIG. 4 and a stay cover shown in FIG. 2 holding the stay to the leg portion.

The stay cover 19 is supported on the medial and lateral sides of the leg portion 11 and forms pockets therewith, as shown best in FIGS. 2 and 10. The stay cover 19 is formed of a separate sheet attached via stitches 23 extending through the sheet and the material of the leg portion 11. Preferably, the pockets formed by the stay cover 19 each have a shape congruent with the shape of one of a pair of stays 15, as will be described hereinafter. More particularly, each of the pockets formed by the stay cover 19 extends downwards along the medial or lateral side of the lower leg 50 and curves forward along a portion of the foot 52 after passing over the ankle. Other shapes are possible for the pockets formed by the stay cover 19 depending upon the desired size and shape of the stays 15. The stay cover is preferably constructed of an outer unbroken-loop material (UBL) that is VELCRO hook 88 compatible, a urethane backing and an inner, elastic liner preferably of DARLINGTON (MOORE) CG25530-1090 162 Black 62 elastic, as shown in FIG. 8. Although use of the stay cover 19 is preferred, the stays 15 can also be fastened, or secured, against the leg portion 11 using other devices, such as additional straps, pads of hook material on the stays or an overlying elastic sleeve.

Figures 4, 5:
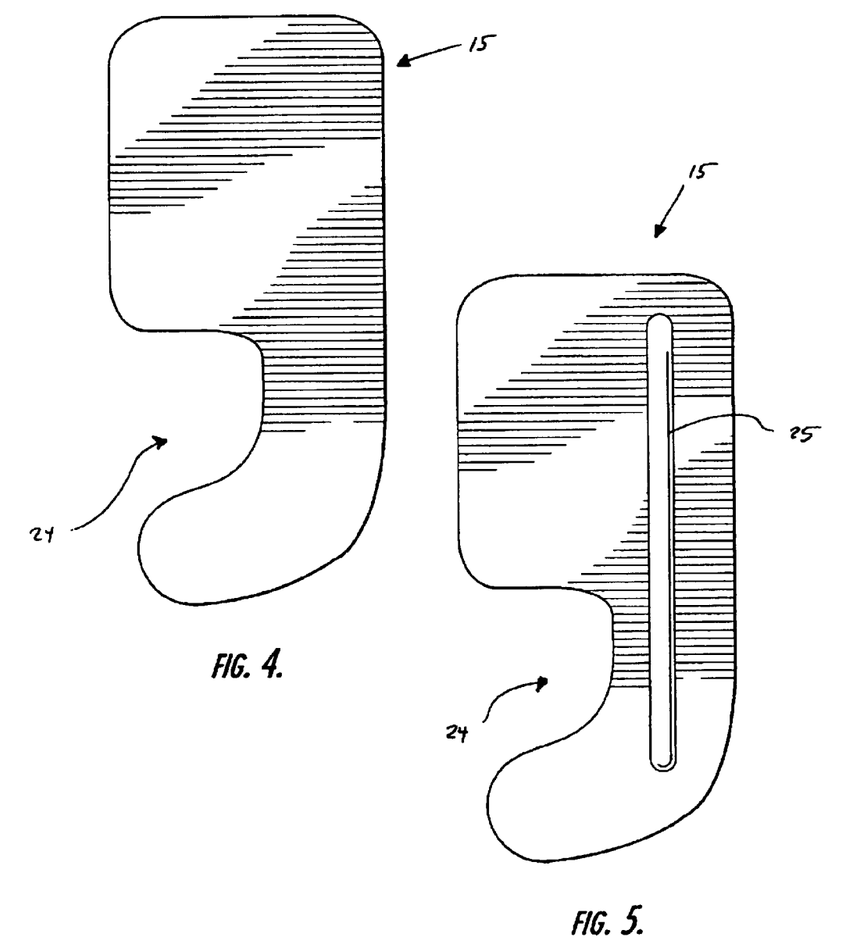
FIG. 4 is a side elevation view of a relatively rigid stay of the present invention for use with the ankle brace shown in FIG. 1.
FIG. 5 is a side elevation view of another stay of the present invention including a reinforcement rib.

In the illustrated embodiment, each of the stays 15 has an "L-shape" (as shown in FIGS. 4 and 5) and is configured to extend along a portion of the lower leg 50, over the ankle and a portion of the foot 52 (as shown in FIGS. 2 and 10) within a respective one of the pockets formed by the stay cover 19, as shown in FIG. 8. In this manner, the stays 15 are rendered relatively immobile on the medial and lateral sides of the brace 10 and provide rigid reinforcement for the ankle. In addition, the stays 15 act as a supplement to the wearer's proprioception, allowing the wearer to sense and react to excessive inversion or eversion of the foot 52. Preferably, the stays 15 are injection molded from a low density polyethylene, although other materials could also be used, such as lightweight metals, plastics or wood. The stays can also be stamped from a synthetic sheet material and can have other shapes depending upon the amount and location of needed support. Preferably, each of the stays has a thickness of about 0.090 inches.

Optionally, each of the stays 15 may be shaped to accommodate the shape of the wearer's leg, ankle and foot anatomy. For instance, the stay may be curved at its upper end to follow the curve of the lower leg 50, or may define a notch 24 at its rear (posterior) edge sized and shaped to correspond to the malleolus of the wearer. As another option, each of the stays 15 may include a rib 25 (or ribs) that further stiffen the stay against bending loads, as shown in FIG. 5. The rib or ribs may have different geometries and configurations, but preferably the rib is a single ridge extending along the portion of the stay adjacent to the lower leg 50 and ends at the portion of the stay over the ankle. Other configurations could include several parallel ribs extending along the leg-adjacent portion of the stay, and along the foot-adjacent portion. Preferably, the rib 25 or ribs have a relatively low profile that minimizes the bulkiness of the stays 15 and the stay cover 19, thereby providing strength while still allowing use of the brace 10 with conventional footwear. For instance, the rib could be an additional 0.090 inches of thickness over the preferred 0.090 inches of thickness of the base stay material, for a total of 0.180 inches.

Figure 6:
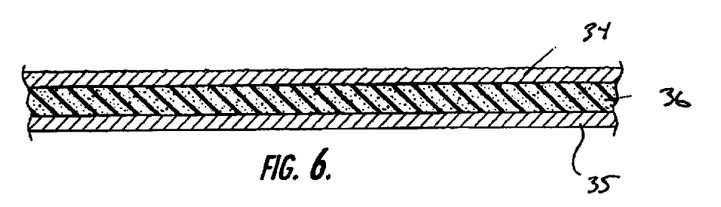
FIG. 6 is a sectional view of a laminate material used to construct a strapping system of the ankle brace shown in FIG. 1.

The foot portion 12 and cross-straps 13 are preferably constructed from a single piece of laminate material and together form a strapping unit. Preferably, the single piece of laminate material is a two-axis stretch urethane laminate with an inner ply 34 of lightweight sueded polyester stretch French terry, a lightweight polyester outer jersey ply 35, and a core polyurethane foam 36 sandwiched between the inner and outer plies, as shown in FIG. 6. The preferred thickness of the single piece laminate material is about 0.05 to 0.11 inches at 0.5 psi. Other laminate materials could also be used, provided that material is thin enough to allow the wearer to also wear a conventional shoe over the foot portion 12, and strong enough to provide support, along with the leg portion 11 and the stays 15, against inversion and eversion of the foot. Preferably, however, the laminate also includes the moisture-wicking, padding and elastic qualities of the above-described terry/foam/jersey laminate. The foot portion 12 and cross-straps 13 may also be constructed of separate pieces of laminate material joined together; although not as preferred as the single-piece strapping unit due to the need for stitching and/or overlap, the multi-piece strapping unit would still have moisture wicking properties.

Figure 3:
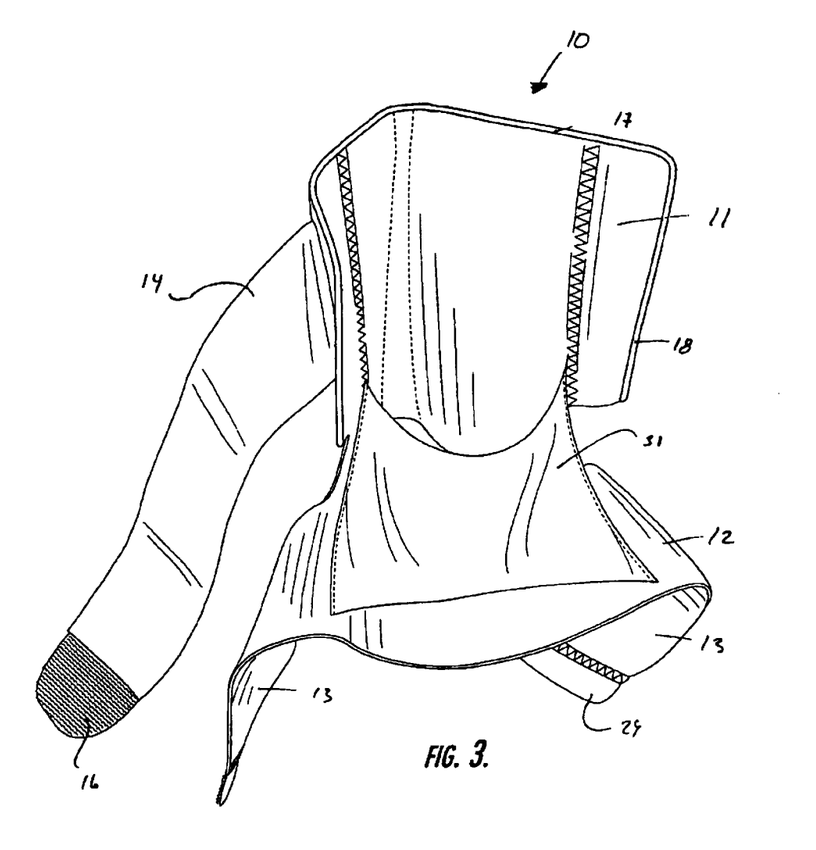
FIG. 3 is yet another perspective view of the ankle brace of FIG. 1, but opened and ready to receive the ankle of the wearer.

Similar to the leg portion 11, the foot portion 12 of the illustrated embodiments has the shape of a cuff formed of a sheet material (the aforementioned laminate), except that the cuff extends under the foot 52 and upwards on both the medial and lateral sides of the foot to become the cross-straps 13 as shown in FIGS. 1–3 and 9–11. A rearmost end of the foot portion attaches near the ankle to the medial and lateral sides of the leg portion 11 via lines of stitching 26. Optionally, the leg portion 11 and foot portion 12 together define a heel opening 27 that receives a heel 54 of the wearer's foot 52. In addition, the forward or anterior end of the foot portion 12 defines a toe opening 28 through which extends the toes 55 of the wearer's foot 52. Advantageously, the heel and toe openings 27, 28 facilitate use of the brace 10 with most conventional footwear, which typically is not adjustable in the front-to-back direction. Optionally, the ankle brace 10 may include a tongue 31 constructed of a flexible material, such as LYCRA, that extends between the medial and lateral sides of the foot portion 12 and over the instep 56 of the foot 52, as shown in FIG. 3. The tongue 31 serves to hold the opposing medial and lateral sides of the foot portion together and can protect the instep 56 of the foot somewhat from chafing by the cross-straps 13. In addition, the tongue could also extend over the upper ankle or leg 50.

Each of the pair of cross-straps 13 extends at one end from, and as part of the same piece of material as, a respective medial or lateral side of the foot portion 12. The other end of each of the pair of cross-straps 13 includes a hook material pad 29. When the ankle brace 10 is being worn, the cross-straps 13 extend upwards over the respective medial and lateral top surfaces of the foot 52 and cross over each other at the instep and/or anterior ankle.

After crossing, each of the cross-straps 13 wraps around, and attaches to, an opposite side of the leg portion 11 via the hook material pad 29, as shown in FIGS. 1 and 9. Each hook material pad 29 attaches to the loop material on the outside of the stay cover 19. The lateral one of the cross-straps 13 extends upwards from the lateral side of the foot 52 and attaches to the medial side of the leg portion 11, while the medial one of the cross-straps 13 does the opposite. Either one of the straps 13 may be on the outside and the strapping unit will still be equally effective at securing the ankle brace 10.

During use, the wearer pulls apart the opposing front edges 18 of the leg portion 11 to the configuration illustrated in FIG. 3 or 11, and slides the foot 52 into the foot portion 12, under the flexible tongue 31 (if present such as in the embodiment in FIG. 3), until the toes 55 extend through the toe opening 28 and the heel 54 extends through the heel opening 27. Meanwhile the leg portion 11 is pulled up onto about the mid-point of the lower leg 50. The cross-straps 13 are crossed over each other at the instep 56 and anterior portion of the ankle. The cross-straps are pulled tight and the hook material pad 29 at the end of each of the cross-straps is attached to the hook-engageable stay cover 19 on the medial or lateral side of the leg portion 11 opposite from the side of the foot portion 12 on which the respective strap originated. At the top of the leg portion 11, the free end of the lower leg strap 14 is threaded outwards through the buckle 33 on the opposite one of the opposing edges 18 and wrapped back on itself. The leg strap 14 is extended around the leg portion 11, pulled tight to hold the edges 18 together, and the hook material 16 on its free end is secured to the adjacent loop material on the hook engageable stay cover 19. The wearer is then free to insert the foot 52 and ankle brace 10 into a running shoe, or other athletic footwear for support during activities.

Among other advantages, the ankle brace 10 of the present invention supports the wearer's ankle while having minimal bulk and therefore being useable with conventional footwear. Further, the use of a single piece of laminate material for the strapping system eliminates the need for overlapping material or fasteners to attach the cross-straps 13 to the foot portion 12. Elimination of the overlap and fasteners further reduces bulk and facilitates use of the ankle brace 10 with footwear. Use of a laminate material with wicking properties keeps the ankle, foot 52 and lower leg 50 of the wearer dry during athletic activities. The optional rib 25 on each of the stays 15 improves the stiffness of the stay without adding appreciable weight or bulk to the ankle brace 10.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. An ankle brace for comfortably supporting an ankle of a wearer by inhibiting motion between a foot and lower leg of the wearer, while simultaneously wicking moisture away from the foot, snide and lower leg of the wearer, said ankle brace comprising:

a leg portion constructed of a flexible sheet material configured to embrace the lower leg of the wearer and to extend distally along the lower leg to the ankle, said leg portion defining an opening for receiving the lower leg of the wearer;

lateral and medial stays constructed of a relatively rigid material and configured to extend along portions of the lower leg, ankle and foot of the wearer, said lateral and medial stays attached to respective lateral and medial sides of the leg portion so as to inhibit relative motion between the foot and lower leg of the wearer; and a strapping unit consisting essentially of a single piece of moisture-wicking, laminate sheet material forming a foot portion and a pair of cross straps, said foot portion coupled to the leg portion at the ankle and configured to extend along and under at least portions of the foot, said cross-straps configured to extend upwards from the foot portion, cross over each other at the top of the foot and attach to the leg portion so as to further inhibit relative motion of the foot and lower leg while the laminate sheet material wicks away moisture from the wearer's foot, ankle and lower leg.

2. An ankle brace of claim 1, wherein at least one of the stays includes at least one stiffening rib.

3. An ankle brace of claim 2, wherein the rib extends vertically along the stay.

4. An ankle brace of claim 1, wherein the laminate material includes an inner moisture-wicking ply, an outer elastic ply and a foam core between the inner and outer plies.

5. An ankle brace of claim 1, wherein the leg portion includes lateral and medial pockets configured to hold the lateral and medial stays.

6. An ankle brace of claim 1, wherein the flexible sheet material of the leg portion is a laminate material having moisture-wicking properties.

7. An ankle brace of claim 5, wherein the leg and foot portions are stitched together at the ankle.

8. An ankle brace of claim 1, wherein the stays define a notch sized and shaped to comfortably receive a malleolus of the wearer.

9. An ankle brace of claim 1, further comprising a lower leg strap configured to encircle and bind the leg portion to the lower leg of the wearer.

10. An ankle brace of claim 1, wherein the leg portion includes an outer surface having one of a loop and hook material disposed thereon, and each of the straps have an end with the other one of the loop and hook material disposed thereon.

11. An ankle brace of claim 1, wherein the foot portion defines a heel opening.

12. An ankle brace of claim 1, wherein the foot portion defines a toe opening.

13. An ankle brace for comfortably supporting an ankle of a wearer by inhibiting motion between a foot and lower leg of the wearer, while simultaneously wicking moisture away from the foot, ankle and lower leg of the wearer, said ankle brace comprising:

a leg portion constructed of a flexible sheet material configure to embrace the lower leg of the wearer and to extend distally along the lower leg to the ankle, said leg portion defining an opening for receiving the lower leg of the wearer;

a lateral and medial stays constructed of a relatively rigid material and configured to extend along portions of the lower leg, ankle and foot of the wearer, said lateral and medial stays attached to respective lateral and medial sides of the leg portion so as to inhibit relative motion between the foot and lower leg of the wearer and wherein at least one of the stays includes at least one stiffening rib; and a strapping unit consisting essentially of a single piece of moisture-wicking, laminate sheet material forming a foot portion and a pair of cross straps, said foot portion coupled to the leg portion at the ankle and configured to extend along and under at least portions of the foot, said cross-straps configured to extend upwards from the foot portion, cross over each other at the top of the foot and attach to the leg portion so as to further inhibit relative motion of the foot and lower leg while the laminate sheet material wicks away moisture from the wearer's foot, ankle and lower leg.

14. An ankle brace of claim 13, wherein the rib extend vertically along the stay.

15. An ankle brace of claim 13, wherein the leg portion includes lateral and medial pockets configured to hold the lateral and medial stays.

16. An ankle brace of claim 13, wherein the stays define a notch sized and shaped to comfortably receive a malleolus of the wearer.

17. An ankle brace of claim 1, wherein the leg portion is configured to extend around between an 8 inch and 10 inch perimeter of the lower leg of the wearer above the wearer's malleoli.

18. An ankle brace of claim 1, wherein the stays have a thickness of about 0.090 inches to 0.180 inches.

19. An ankle brace of claim 1, wherein the single piece of sheet material of the strapping unit has a thickness of about 0.05 inches to 0.11 inches.

20. An ankle brace of claim 13, wherein the single piece of sheet material of the strapping unit has a thickness of about 0.05 inches to 0.11 inches.

* * * * *